(12) United States Patent
Odefey

(10) Patent No.: US 7,547,554 B2
(45) Date of Patent: Jun. 16, 2009

(54) METHOD AND DEVICE FOR THE DETECTION OF VERY SMALL QUANTITIES OF PARTICLES

(75) Inventor: Constantin Odefey, Hamburg (DE)

(73) Assignee: Friedrich Werner, Hamburg (DE)

( * ) Notice: Subject to any disclaimer, the term of this patent is extended or adjusted under 35 U.S.C. 154(b) by 406 days.

(21) Appl. No.: 10/572,868

(22) PCT Filed: Sep. 9, 2004

(86) PCT No.: PCT/EP2004/052109

§ 371 (c)(1),
(2), (4) Date: Mar. 22, 2006

(87) PCT Pub. No.: WO2005/031325

PCT Pub. Date: Apr. 7, 2005

(65) Prior Publication Data

US 2007/0054417 A1    Mar. 8, 2007

(30) Foreign Application Priority Data

Sep. 25, 2003   (DE) ................................ 103 44 924

(51) Int. Cl.
*G01N 21/03* (2006.01)
(52) U.S. Cl. ...................... 436/165; 435/7.1; 435/7.21; 435/7.25; 435/7.31; 435/7.32; 435/7.94; 435/287.1; 435/287.2; 436/512; 436/513; 436/517; 436/519; 436/536; 436/537; 436/540; 436/10; 436/164; 422/55; 422/68.1; 422/73

(58) Field of Classification Search .................. 435/7.1, 435/7.21–7.32, 287.1, 287.2; 436/512, 513, 436/517, 518, 519, 523–531, 539, 540, 541, 436/10, 63, 536, 537, 164, 165; 422/55, 422/68.1, 73

See application file for complete search history.

(56) References Cited

U.S. PATENT DOCUMENTS

| 4,444,879 A | * | 4/1984 | Foster et al. ................ 435/7.95 |
| 5,100,805 A | | 3/1992 | Andris et al. |
| 5,534,441 A | * | 7/1996 | Miyazaki et al. ............ 436/517 |

OTHER PUBLICATIONS

"Sorting Single Molecules: Application to Diagnostics and Evolutionary Biotechnology" Proceedings of the National Academy of Sciences of USA, National Academy of Science, Washington, US, vol. 91, Jun. 1994, pp. 5740-5747, XP002029412, Eigen M. et al.

* cited by examiner

*Primary Examiner*—Gailene R Gabel
(74) *Attorney, Agent, or Firm*—Joseph T. Guy; Nexsen Pruet, LLC

(57) ABSTRACT

The invention relates to a method and a device for detecting very small quantities of particles. The inventive method is based on a detection of antigen-antibody reaction products and provides a very high detection sensitivity all the way to the femtomolar or attomolar range.

8 Claims, 3 Drawing Sheets

METHOD AND DEVICE FOR THE DETECTION OF VERY SMALL QUANTITIES OF PARTICLES

FIELD OF THE INVENTION

The present invention provides a method and a device for the detection of very small quantities of particles by the detection of antigen-antibody-reaction products, the method having a very high detection sensitivity down to the femtomolar or attomolar range.

BACKGROUND AND PRIOR ART

Several methods for detection of small quantities of particles are known in the art, for example, nephelometric and turbidimetric methods as well as methods referred to as dynamic-light-scattering (DLS).

In nephelometric and turbidimetric methods, the Tyndall effect is used in which the illumination of a small particle produces wide-angle scattered light. The scattering of the light can be determined, either by measuring the decrease of intensity of the incident light beam after passing through the scattering medium or by determining the intensity of the laterally deflected light. The former case is referred to as the method of turbidimetry or measurement of extinction, and the latter case as nephelometry proper, or tyndallometry.

Methods referred to as dynamic-light-scattering (DLS) methods afford another approach. In these methods, just one (or a few) points on the light sphere surrounding the particle are observed but in addition, the brightness modulation caused by the Brownian movement is analysed. By focusing on a tiny monitoring volume, one attempts to reduce the interference due to the superposition of scattered light from several particles. Consequently, a particle passes very quickly through a tiny illuminated volume, so that the analysing optoelectronics must detect significant fluctuation frequencies. A large amount of information is supplied by the complex signal processing, so that these systems are only conditionally useful for quantitative analysis.

The detection methods of the prior art exhibit further disadvantages. It should first be mentioned that, although the detection sensitivity of the methods just described has strongly increased in recent years, there still is a strong need in the most diverse fields for detection methods having higher sensitivity. Furthermore, the detection methods of the prior art still require comparatively large amounts of samples, which particularly in methods of medical technology may put stress on the person being examined.

It is an object of the present invention, therefore, to provide a method for the detection of small quantities of particles which exhibits a higher sensitivity than the methods of the prior art. Furthermore, such a method should require less dilution of the sample and/or a lower minimum amount of sample, should be suitable for sample analyses on a larger scale, and after elementary training should also be realisable by personnel without special prior experience. Furthermore, it is an object of the invention to provide a device for the detection of small quantities of particles.

This object is attained by providing a method for the detection of small quantities of particles by the detection of antigen-antibody precipitates, the method comprising: providing a sample fluid that essentially contains particles with a given maximum particle size, the particles having at least two antibody binding sites; providing a fluid containing antibodies that contains essentially particles with a given maximum particle size; contacting the sample fluid with the fluid containing antibodies, which yields a reaction fluid where in the presence of a particle having at least two antibody binding sites, the antibody can form an antigen-antibody precipitate; directing a light beam through the reaction fluid; detecting a signal by measuring with a photodetector the extinction at the light-dark boundary of the cone of light produced when the light generated by the laser is passing through the measuring cell containing the reaction fluid, the strength of the signal depending on the size and number of the antigen-antibody precipitates formed.

The present invention further provides a device for the detection of small quantities of particles which comprises: a light source, a measuring cell, and a photodetector that is designed for measuring the extinction at the light-dark boundary of the cone of light produced when the light generated by the laser is passing through the measuring cell containing the particles in a fluid. The light scattered forward forms a cone, and the photodetector is aimed at the light-dark boundary thereof. Laser and photodetector are essentially axially aligned, though offset in such a way that the laser beam very narrowly passes by the photodetector.

DETAILED DESCRIPTION OF THE INVENTION

Figure 1A:
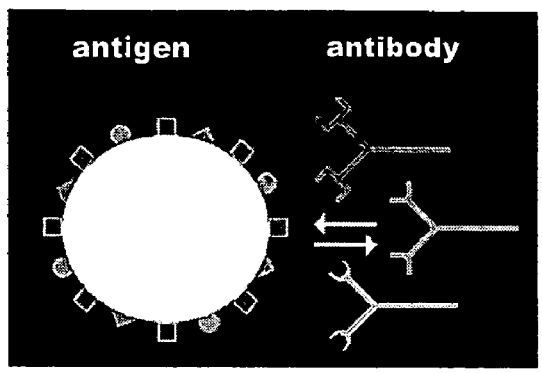
FIGS. 1A-1D schematically illustrate the processes when forming an antigen-antibody precipitate using a divalent antibody.

In numerous experiments leading to the present invention, a method was developed in which the sensitivity exceeds the sensitivity of comparable methods of the prior art by a factor of 1000. This strong increase of sensitivity is due to a modified physical detection method in association with matching analytical sample preparation in which a signal is detected by measuring with a photodetector the extinction at the light-dark boundary of the cone of light produced when the light generated by the laser is passing through the measuring cell containing the reaction fluid.

Furthermore, the present invention allows the volume of the measuring cell to be reduced by a factor of about 30 to 50. Whereas in methods of the prior art, measuring cells with volumes in the range of, for example, 1.6 ml are required, in the method according to the invention measuring cells having a volume in the range of microliters (for example, 40 µl) can be used. This is an important advantage, since each sample has to be diluted in order to yield a uniform matrix which, for example, has the same transparency, viscosity, etc., so that in a method according to the invention, a sample has to be diluted less strongly than in methods of the prior art.

Furthermore, with the method according to the invention, it is possible to reduce the minimum amount of sample required. Whereas methods of the prior art require more than 100 µl, in the methods according to the invention amounts of sample many times smaller will suffice (for example, 3.5 µl).

In the present application, the term "particles" denotes any three-dimensional entity having a refractive index different from that of the supporting medium.

The term "precipitation" as used in the present application describes the process when a reaction of soluble antigens with specific antibodies yields an antigen-antibody-complex having a lower solubility in the solvent used than the antigen and antibody used, which reaction at first results in turbidity of the reaction mixture and, subsequently, in sedimentation of this antigen-antibody-complex.

The method according to the invention allows small quantities of particles to be detected. For example, by using the method according to the invention, a limit of detection in the range of femtograms and attograms per liter could be achieved with low-molecular-weight substances, i. e., with substances having a molecular weight of less than 500 g/mol, whereas up to now, the detection limit usually is in the range of micrograms, nanograms, or picograms per liter. The limit of detection is higher with substances having a molecular weight in the range above 500 g/mol, for example, the limit of detection is about 300 femtograms/liter with substances having a molecular weight of 150,000 g/mol (e. g., IgG antibodies). This means that the sample fluid may contain particles in an order of magnitude of femtomoles or attomoles per liter.

In a first step of the method according to the invention, an analyzing fluid is provided that contains particles having a given maximum particle size. There are, for example, two ways to achieve this. According to a first option, initially a fluid is provided that essentially contains only particles having a given maximum particle size, and subsequently, a sample that essentially contains particles having a given maximum particle size is added to the fluid. According to a second option, the sample fluid can be obtained by initially providing a fluid, adding a sample to the fluid and, subsequently, removing particles that exceed a given particle size.

The maximum particle size of the particles in the analyzing fluid and in the other fluids that essentially contain only particles of a given maximum particle size can be selected depending on the desired application. With many common antibodies, particles may be separated that are larger than 20-450 nm, more preferably larger than 100-300 nm, and particularly larger than 200 nm. This separation can be effected, for example, with filters having a suitable, corresponding pore size of 20-450 nm, more preferably 100-300 nm, and particularly 200 nm or by other methods known to persons skilled in the art. If agglutination, as an approximation, is considered as a surface, then halving the filter size is affecting the number of molecules that will yield detectable reaction products, in a quadratic proportion. If, for example, a 100-nm filter is used instead of a 200-nm filter, then only about a quarter of the number of antigen-antibody molecules that is required when using a 200-nm filter must now react with each other in order to achieve a detectable result. Furthermore, it will, for example, be possible to detect antigen-antibody-antigen trimers when using 25-nm filters. When using filters having such a small pore size, particular care must be exercised, since a few molecules are sufficient to lead to a detectable reaction.

Figure 1B:
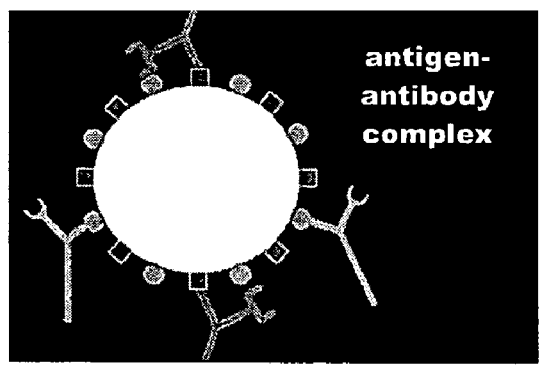
Figure 1C:
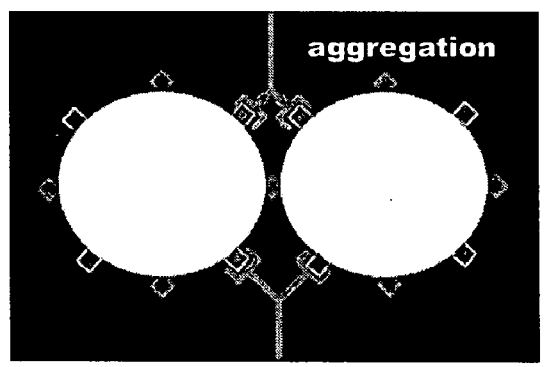
Figure 1D:
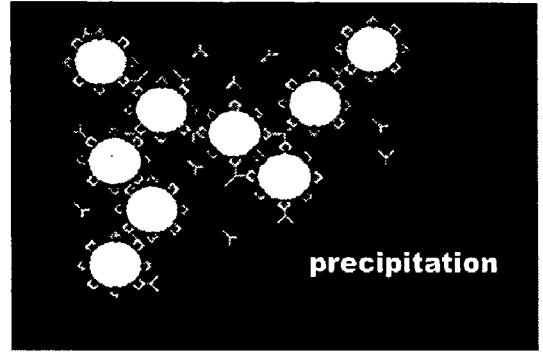

For a cross-linking reaction to occur, the particles contained in the analyzing fluid must have at least two antibody binding sites and, therefore, can act as an antigen. FIGS. 1A to 1D schematically illustrate that exogenous substances or particles such as bacteria, viruses, toxins, and proteins act as antigens and react with an antibody according to the "lock-and-key principle" (FIG. 1B). A divalent antibody such as an IgG antibody will then bind to two antigens (FIG. 1C). Since each antigen can bind several antibodies, a cross-linking (precipitation) occurs which is detected by the method according to the invention (FIG. 1D). An analogous precipitation occurs with antibodies having a higher binding order. If the antigen used provides a larger number of antibody binding sites, there is the advantage that the cross-linking reaction will proceed more reliably.

The method according to the invention is suitable for any antigen so long as it has at least two antibody binding sites. Preferably, the particles tested should be larger than about 10 nanometers, and at the same time they should be smaller than the maximum particle size selected. Molecules which are smaller than 10 nm can act as haptens. Haptens are incomplete antigens, i. e. contain an antigenic determinant but are not large enough to trigger an immune response or induce agglutination unless coupled to a carrier. These low-molecular-weight substances are in fact highly specific to the paratope binding site of the antibody, but they do not protrude far enough from this binding site for a second antibody to be able to bind to them. They block the particular antibody without the possibility for a cross-linking reaction to occur. Larger antigens such as bacteria must be chemically or physically destroyed prior to the measurements, which can be achieved with several methods known to persons skilled in the art, for example, by ultrasound, acids, bases, or surfactants. This provides the advantage that in this way dozens of fragments are obtained from a single bacterium, and it is no longer necessary to let individual bacteria agglutinate. The fragments thus obtained—for example, surface proteins—in turn represent smaller antigens and may give rise to a specifically measurable reaction with suitable antibodies.

Furthermore, the antigen should essentially be soluble in the buffer used, and should have a low adsorption affinity for the walls of the devices and filters used.

The method according to the invention further comprises providing a fluid containing antibodies.

In the method according to the invention, in principle any antibody desired can be used. Antibodies which proved to be particularly advantageous for a method according to the invention are, for example, the divalent immunoglobulin G (IgG) or the decavalent immunoglobulin M (IgM). According to a method known to persons skilled in the art, antibodies with a well-defined specificity can thus be obtained. Other antibodies which belong to a different class of antibodies can also be used, depending on the type of the particles to be detected. Here the antibodies can be monoclonal or polyclonal. When using monoclonal antibodies, two monoclonal antibodies directed to different antigens can be introduced to produce precipitation. In the same way as mentioned above with respect to the antigen, the antibody should also be essentially soluble in the buffer used, and have a low adsorption affinity for the walls of the devices and filters used.

In the method according to the invention an undesirable, overly large excess of antigens or antibodies can be avoided in different ways, for example by suitable dilution series. Otherwise, such an overly large excess of antigens or antibodies could lead to an inhibition of precipitation (the so-called "prozone phenomenon"), since in the presence of a large excess of antibodies, each epitope (antigen binding site) will only bind monovalently to a single antibody, and a cross-linking is no longer possible, or since in the presence of an overly large excess of antigens, often trimers are formed from an antibody molecule and two antigen molecules.

Both for preparation of the sample fluid and for preparation of the fluid containing antibodies, in principle any gas or liquid can be used as the fluid. Preferably, the fluid is a liquid. Often the liquids are water or buffer solutions known in the prior art, such as PBS (phosphate buffered saline), particularly so in analytical methods based on a biochemical reaction. In principle, the liquid can also be any other transparent liquid, for example, liquid hydrocarbons, acids or bases.

In the method according to the invention, in a next step the analyzing fluid is contacted with the fluid containing antibodies, where in the presence of an antigen the antibody can form an antigen-antibody precipitate, which now, for example, can be detected with the device according to the invention.

Beyond that, an interest often exists to detect the presence of haptens in a sample. Haptens are incomplete antigens, i. e., they are too small to bind to more than one antibody. In particular, haptens can be pharmaceutical products, drugs, pesticides, environmental poisons, steroid hormones or mycotoxins. Haptens specifically bind to antibodies. However, they only block the paratope binding site of the antibody without the possibility for a chain reaction to occur. The minimum size of immunogens (complete antigens) is 5 to 10 kDa, i. e., >30 amino acid residues or a length of >3 nm, because starting from this size, at least two antibody molecules can couple with these antigens via appropriately available epitope binding sites, and trigger a chain reaction often leading to precipitation.

A determination of haptens can be effected, for example, with hydrophilic macromolecular multispacers (hmM) or with related compounds known by persons skilled in the art. Hydrophilic macromolecular multispacers are known in the prior art, and are comprised of a hydrophilic macromolecule such as albumin. The same hapten molecules or different hapten molecules are chemically coupled to this hydrophilic macromolecule via spacers known in the prior art. If a hydrophilic macromolecular multispacer has at least two identical hapten molecules, it can be used for precipitation. Such a molecule can be used for an antibody screening test which is based on a displacement reaction. The haptens thus yield a concept of measurements based on a displacement reaction, exemplified hereinafter, where reaction peaks are only observed in a negative test, i. e., detection of reaction products only occurs via negative tests.

The laser emits a beam through the liquid to be tested, and is used to determine the number and size of the particle present therein. This is done by measuring with a photodetector the extinction at the light-dark boundary of the cone of light produced when the light generated by the laser is passing through the measuring cell containing the reaction fluid (where the photodetector can have an adjustable signal amplification and an adjustable operating point), so that the device acts as a "molecular light barrier". A Q-MAP device as described hereinafter can, for example, detect particle sizes between 20 nm and 5 μm, although this measurement cannot yield any information as to the constitution or composition of the particles detected. Laser and photodetector are almost coaxial. The laser beam very narrowly passes by the photodetector. The light scattered forward forms a cone, and the photodetector is aimed at the light-dark boundary thereof.

Each particle that is present in a fluid in the measuring cell and passes the laser beam generates a signal, the numbers of signals corresponding to the statistical distribution of the particles in the measuring cell. When particles, even smallest particles, pass through the cone of light in the focus of the laser, they block light as if casting a shadow. The change in original brightness (without the particle shadow) is measured. A fast computer, for example, a Pentium computer, can distinguish up to 10,000 particle passages per second. Small particles move faster than large ones, so the transit time is a direct measure for particle size.

If several particles are present in the laser beam at the same time, only the largest one is measured. Using the different velocities with which the particles pass the laser beam, the corresponding particle sizes can be calculated via the Stokes-Einstein equation well-known to persons skilled in the art. In this measurement, not so much the absolute particle size but, rather, the changes in particle size (caused by particle growth) are of importance. The particular filter used serves as the measure for determining the onset of particle growth. The larger the filter pores, the larger the precipitates must grow in order to be distinguished from "background noise". With 100-200 nm filters, very few growing particles will suffice to generate a detectable signal. Since the particles are statistically distributed, particle growth will always also happen in the laser focus that is in the center of the measuring cell.

The velocity with which the particles pass thorough the laser beam is detected by measuring the transit time needed for the particle to pass through the beam (from the start to the end of brightness change).

It can be seen here that in a cleaner solution, it will be the more likely that individual, separate particles exist in the laser beam; or, the more contaminated a solution, the more signals will be superimposed leading to decreased sensitivity.

The signal strength depends on the size and the number of the antigen-antibody precipitates.

At a constant concentration of antibodies, the decrease of the signal measured is directly related to the concentration of antigens.

In a detection procedure according to the invention, one can proceed as follows: All the fluids to be tested are injected into the measuring cell through filters having a given pore size, so that in a separate observation of the analyzing fluid or antibody fluid, only signals will appear in the evaluation that are indicative of particles smaller than a given particle size. In the method according to the invention, both the antibodies used and the antigens used have particle sizes below said size limit, and thus are smaller than the pore size of the filters used for separation (for example, smaller than 200 nm), so that they are not removed during the separation.

Figure 2A:
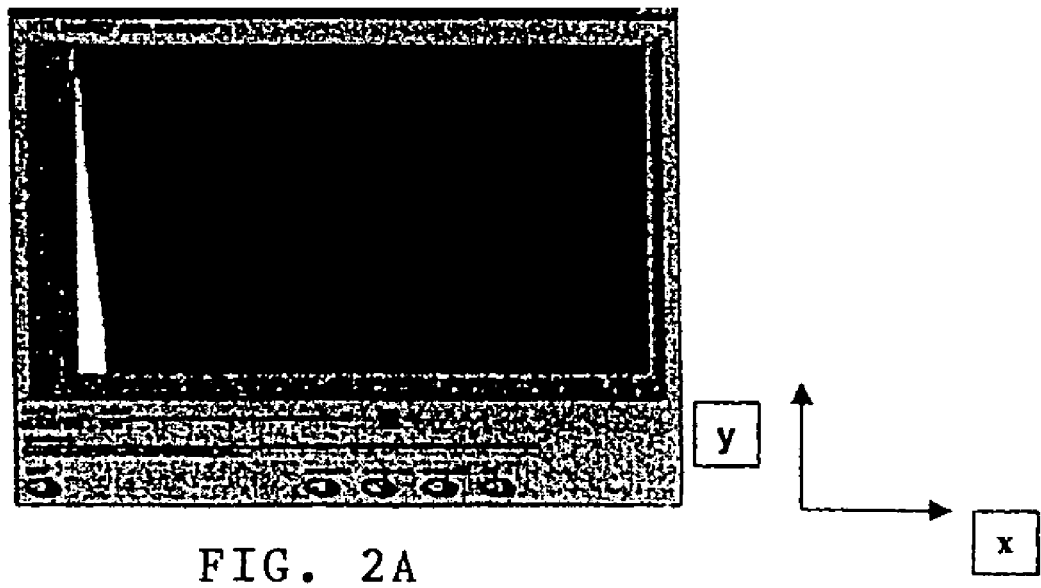
FIG. 2A illustrates a result of detection using the method according to the invention.

An example of such an image recorded with an analyzing fluid based on NaCl solution is shown in FIG. 2A. In these images, the particle size is illustrated along the x-axis, the number of particles is illustrated along the y-axis. As shown in FIG. 2A, only particles up to a given maximum particle size are present, and fewer particles exist at the larger particle sizes. An analogous detection result will be obtained for the filtered antibody fluid essentially only containing particles of a given particle size (not shown).

Following a simultaneous, separate injection of the analyzing fluid and antibody fluid, a reaction occurs in the measuring cell yielding microprecipitasions, and a detection of the size and number of antigen-antibody precipitates is carried out.

Figure 2B:
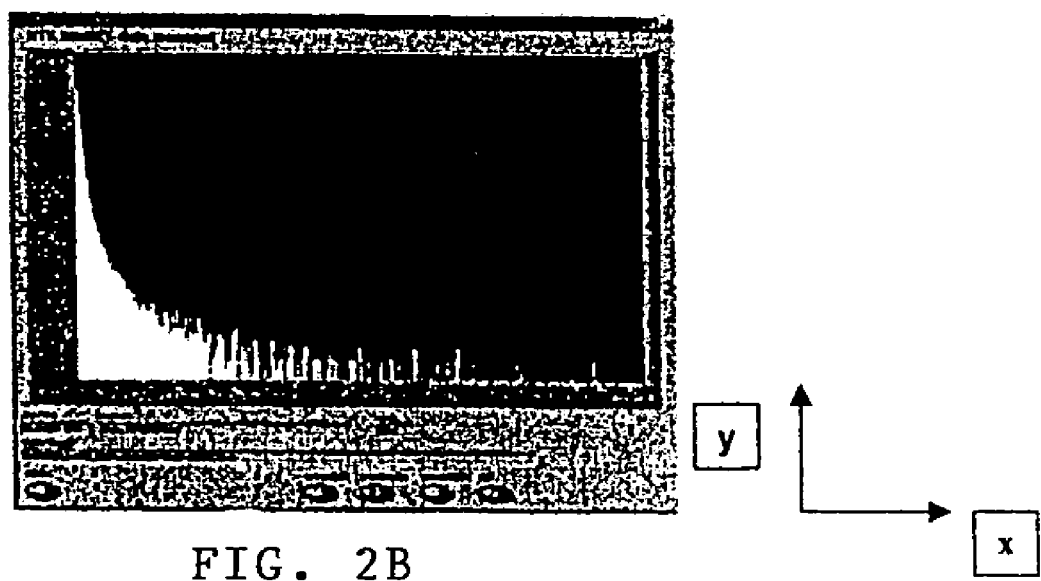
FIG. 2B illustrates a result of detection where the reaction mixture was examined that is obtained upon simultaneous, separate injection of solutions of the sample fluid and the antibody fluid.

A result of such measurements is illustrated as an example in FIG. 2B, where particles are seen to appear which are larger than the given particle size limit of for example 200 nm. The formation of larger particles thus shows that a reaction has occurred. If, to the contrary, no reaction producing larger particles occurs, then the liquid examined is free of the corresponding antigen.

The measurements can be started at any time after filling analyzing fluid and antibody fluid into the reaction cell. According to an embodiment of the present invention, the measurements are started, for example, not earlier than 60 seconds after filling the measuring cell, since slight fluctuations in the rate of injection may result in differences of convection in the measuring cell. After another 60 seconds, for example, maximum precipitation is attained. The decrease of the measured signal occurring thereafter allows an approximate quantitative detection or estimate of the different antigen concentrations to be made. Here the starting concentrations of both reactants are important. The higher these starting concentrations, the longer will be the time until the decrease of the precipitation maximum becomes detectable.

When practicing the method according to the invention, it is advantageous to use fluids of the highest possible purity, for example, fluids filtered with a filter of suitable pore size of for example 200 nm, prior to their use, in order to eliminate or minimize background noise during detection. In addition, the materials of the devices used in the method according to the invention should release the smallest possible amount of particles. For example, the measuring cell may be made of PTFE (polytetrafluoroethylene). Also, the measuring period may be kept as short as possible in order to keep the materials used (for example, the measuring cell) from releasing particles on a continuing basis.

In addition, the concentrations of the antigen or antibody solutions used should not be so low that an antigen-antibody reaction that occurs will not produce too many precipitates, or precipitates that are too large, since otherwise, several particles may be present at once in the beam, and a transit time would be very difficult to detect. The highest sensitivity of the method according to the invention is in the femtomolar and attomolar range.

It is particularly advantageous that the method according to the invention also yields quantitative or semiquantitative information.

Two methods can, for example, be used to evaluate a quantitative record. In the first method of evaluation, the areas (F) under the curves measured at times t1 and t2 (for example, at times t1=120 seconds and t2=180 seconds) are determined, and a good approximate value $F_N$ is obtained via $$F_N=(F_{t1}+F_{t2})/2,$$

for an area from which a quantitative value for the particle number can then be obtained. At these extremely low concentrations, particle growth is linear, i. e., a doubling of the concentration will, for example, leads to an twice as large area of the measured signal.

An alternative and/or supplementary method for obtaining quantitative information is based on diluting the solutions until reaching the kinetic limit of the bimolecular reaction. At concentrations below 100 attomolar the mean free path of the reactant particles becomes too large (>100 μm) and no detectable precipitation will occur within the given measuring period. At concentrations above 10 nanomolar, steric hindrance starts to occur owing to overly numerous and overly large reaction products, and moreover, the "prozone phenomenon" explained above becomes effective. In a 10 micromolar solution, for example, the mean free path of a particle is merely 100 nm.

The degree of dilution detected at this physical endpoint only depends on temperature and convection, as the viscosity is irrelevant at the high dilutions, e. g., in PBS (phosphate buffered saline). If these two parameters are kept constant, then the degree of dilution of the starting solutions will be a direct measure of concentration of the solutions examined.

An exact quantitative determination of the concentration of samples is possible with the method according to the invention via a calibrating solution containing a known concentration of the protein in question, and procedures known to persons skilled in the art are used to this end.

According to a further embodiment of the method, continuous measurements and/or multiple randomly selected sample measurements of the fluid in the measuring cell can be performed. In this way it is possible in particular to determine the endpoint of the reaction and calculate mean values of the records. Preferably, already prior to adding the antibodies and/or prior to adding the sample the carrier fluid that is essentially free of particles with a particle size above the given value is subjected to measurement; and the result of this measurement is adduced as a reference value for measurements of the precipitate.

In the method according to the invention, relatively small amounts of fluid will suffice; and the efforts made to remove from the fluid used, those substances having a particle size in excess of a given value, can be reduced. For example, the fluid used may also be diverted via valve arrangements through a bypass with a filter removing said substances. The filtering of the fluid used can be carried out over a given, predetermined period prior to introducing the sample, so as to ensure that no substances interfering with the measurements remain in it. Substances in the sample having a particle size in excess of the given value, can be removed more particularly by filters that are integrated into the feed points or disposed upstream of these points. The sample fluid thus obtained may even be filtered during a certain period of time after introduction of the sample in order to remove interfering substances which could enter the fluid with the sample or could arrive from the system of conduits.

According to a further embodiment of the method, the carrier fluid after introduction of an antibody that has or has not led to detect an antigen is refiltered prior to introduction of another antibody. This serves to remove substances which have entered the carrier fluid in the meantime and could interfere with the measurements. It is possible in this way, moreover, to remove a detected reaction product from the fluid used, so as to enable possible further components of the sample to be analysed.

The method according to the invention is suitable for a variety of applications in the areas of water analysis (detection of constituents and harmful substances), food technology (detection of microorganisms, constituents), in biological or medical tests (e. g., the detection of certain DNA or RNA sequences, certain bacteria or allergens (allergy tests)). Applications are possible as well in the areas of hydrophilic macromolecular multispacers, branch DNA sensors or quantitative PCR. The method according to the invention can also be used, more particularly, for the detection of the infectious prion protein $PrP^{Sc}$ in BSE tests. Since in the method according to the invention extremely small quantities of this prion protein can be detected, the method according to the invention is also suitable for a detection of the infectious prion protein $PrP^{Sc}$ in blood.

Furthermore, the Q-MAP measuring method according to the invention provides a rapid, simple possibility for testing the adsorption behaviour of different proteins at a variety of surfaces. Highly polished surfaces could thus be checked nondestructively for a "protein adsorption value", where departures from a rated value would indicate a surface defect. Thus, in this way surface defects can be detected in a simple and rapid way, for example, on thin evaporated metal surfaces.

Furthermore, the complete immobilization of given proteins on surfaces can be tested, which is highly important, for example, in the area of DNA analysis and biochip technology.

A further possible application of the method according to the invention is that of determining the influence exerted by chemicals on a surface. In particular, before-and-after tests detecting changes produced by a surface treatment can for example be envisaged, since a corroded surface has a larger surface area than one not corroded and, thus, a larger quantity of antigen material—for example, proteins—would adsorb on this surface. The amount of free proteins remaining in solution can be detected in this way, for example.

Yet another application is based on the fact that with the method according to the invention one can check the condition of the inner surfaces of hoses and pipes.

After terminating the procedure of the method according to the invention, the antigen-antibody precipitates can be dissolved, for example, with proteinase K, in the case of substances not destroyed by proteinase K (e. g., prions and substances containing no amino acids), and then be subjected to further treatment or testing steps.

It is a further important advantage of the method according to the invention, as described in detail hereinabove, that it also enables quantitative detections to be carried out. In addition, the method can be fully automated, which leads to a distinct reduction of labour cost, so that a method is provided that can be comparably cost-effective.

Furthermore, the method according to the invention enables the detection of very small amounts of pathogens in body fluid or excretions, and particularly in blood. This represents an important advantage, since small amounts of blood, for example a small blood droplet (about 10-20 μl), is readily taken from a finger tip or an earlobe with a capillary tube without the need for a physician or trained nurse. Such tests are readily performed in a pharmacy or in old people's homes or rehabilitation facilities, for example, so that information whether an infection with a given bacterium is present is provided simply and rapidly. It is especially advantageous that both the sampling and the operation of the device according to the invention with which the method according to the invention is realised, do not require any medically trained or highly qualified personnel. Alternatively, other substances in the blood such as drugs or medication can, of course, be detected with such a test using specific antibodies.

While in commercial measuring equipment the ratio of antigen to antibody must not differ by more than a factor of 2-3, measurements are still possible with Q-MAP when the departure from the ideal mixing ratio between antigen and antibody is by a factor of 100. (At a constant concentration of the antibodies, the ideal concentration of antigens was lowered to 1%, and raised to 10,000%. The same was done, conversely, at a constant concentration of the antigens.) Due to this interesting departure from the "Heidelberger curve" in the femtomolar and attomolar range which is caused by the low steric hindrance of the molecules, time-consuming dilution series become unnecessary.

The method according to the invention is particularly suitable for testing pooled samples, which is of particular interest for tests of stored blood (as for HIV or hepatitis) and for BSE test samples. With the method according to the invention, about 50 measurements per hour can be performed, which means that at least 400 tests per day or more than 80,000 measurements per year can be performed when working 8 to 10 hours per day. Thus, 800,000-8,000,000 samples per year can be tested with just a single measuring device when 10-100 samples are pooled for each measurement.

When testing stored blood, 10 different antibodies (against 10 different diseases) can for instance be added to the blood at once in order to establish whether this blood can be used. In the case of a positive reaction, the stored blood must be discarded, since it does not matter whether the contamination is due, for example, to HIV or to hepatitis. Where it is of interest in addition to know which agent has actually triggered the positive reaction, then the antibodies can be introduced individually. By pooling, for example, the blood from 100 containers of stored blood, and using 10 different antibodies simultaneously, one can find out with a single measurement taking about 60 seconds whether the blood from all 100 containers is fit for use.

A test for which such a small amount of product is sufficient and which has an appropriately high sensitivity down to the femtomolar or attomolar range is not known in the prior art up to now, and represents important progress.

In addition, the present invention comprises a computer program product comprising program code means stored in a computer-readable medium, to enable the method according to the invention to be carried out when the computer program product is executed on a computer, a network device or a device, particularly an analytical detection device. The present invention further provides a computer program product comprising program code downloadable from a server, to enable the method according to the invention to be carried out when the computer program product is executed on a computer, a network device or a device, particularly an analytical detection device (for example, a detection device described in the present application).

The present invention further relates to a device for the detection of small quantities of particles also referred to as Q-MAP (quantitative measurement of attomolar precipitation products) device.

Such a device comprises a light source, a laser being used as the preferred light source.

The measuring cell of such a device should be made from a material that essentially does not release particles and that allows passage of a light beam, particularly a laser beam. Such materials are known to a persons skilled in the art. The measuring cell may for example be made of PTFE (polytetrafluoroethylene). The measuring cell has a volume of less than 100 μl, preferably of 30-50 μl, and more particularly of 40 μl.

The device according to the invention more particularly comprises a photodetector adapted for an adjustable signal amplification and an adjustable operating point.

The photodetector can be selected, for example, from the group consisting of thermal detectors, photodiodes, particularly photoconductor detectors, photovoltaic detectors, avalanche diodes, diode arrays, photomultipliers.

A detection device according to the invention more particularly allows particles between 20 nm and 5 μm to be determined.

Additionally, the present invention also provides a kit for the qualitative and/or quantitative detection of a given particle to be detected, for example, a protein or hormone, the given particles having at least two antibody binding sites. The kit comprises a detection device, as described hereinabove, at least one antibody able to specifically bind to the given particle, and at least one suitable fluid for receiving the sample. Such a kit can be designed for a user's particular needs, and contains matching components as well as a corresponding description for the user who instantly and very easily will be able to carry out detections according to the invention with this kit. For example, such a kit can be used for detecting a particular pathogen in a small amount of blood, or for surface studies in the applications described hereinabove.

Figure 3:
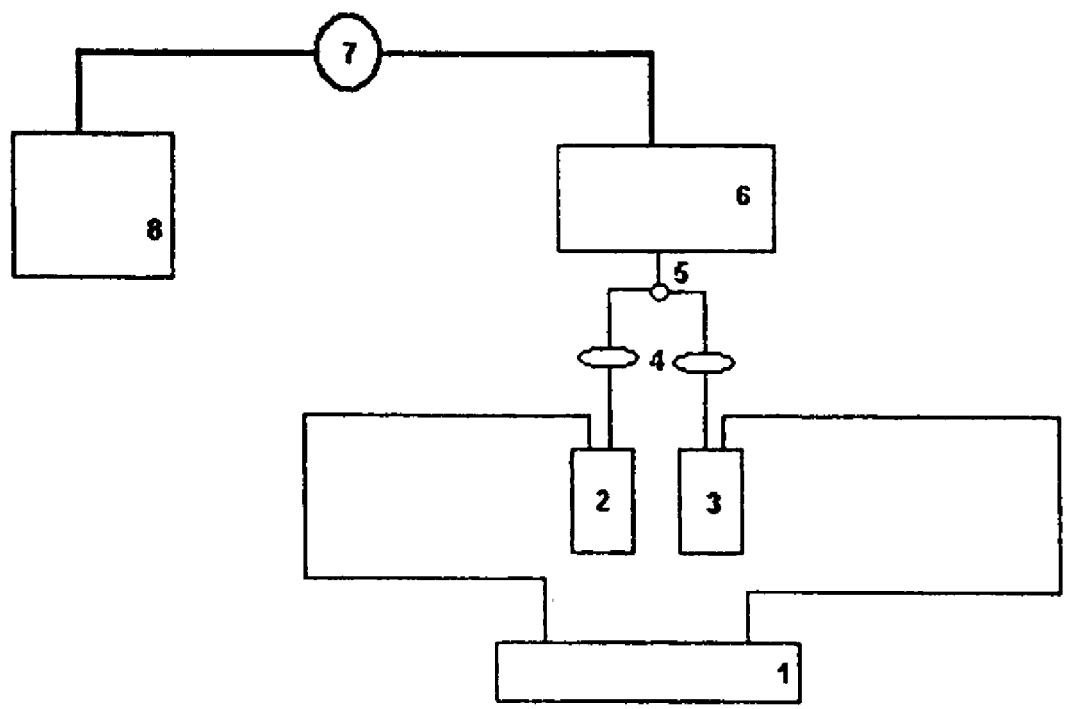
FIG. 3 shows a schematic drawing of an installation for practicing the method according to the invention.

In the following, the invention will be explained in greater detail with the aid of FIG. 3, the appended schematic, an exemplary but not limiting drawing of an installation for carrying out the method according to the invention.

The sample changer 1 can inject different antigen solutions (e. g., blood samples) as well as different antibody solutions into the respective mixing vessels 2 and 3 so that a sample can be tested consecutively for several possible germs. The mixing vessels 2 and 3 for the antigen and antibody solutions, respectively, are useful, not only for dilution of the respective solutions but also for rinsing the measuring cell with buffer (PBS) or antibody solution.

Filters 4 are exchangeable and have a pore size of, for example, 200 nm. Valve 5 can be switched so that the solutions can flow separately or jointly into the measuring cell 6 where detection with the detection device is carried out continuously, a single time, or a number of times on a random basis.

Pump 7 is, e. g., a small vacuum pump for drawing up all the solutions. It is coordinated with valve 5, and after measurements pumps the contents of the measuring cell to the waste receptacle 8. This receptacle may be provided, e. g., with a disinfecting or germicidal liquid so that all potentially hazardous substances can be rendered harmless at once.

If the antibody that is introduced reacts with an antigen from the sample to form an antigen-antibody precipitate, particles are formed that have a particle size that exceeds the given value. These precipitates generate a signal which significantly differs from the signals from particles having a particle size below the given value that may still be present in the carrier fluid. Consequently, these reaction products are uniquely detected by the detection device. It follows from the detection results that a particular substance is present in the sample and, where required, its concentration can also be determined according to the methods described hereinabove.

If, after injection of a first antibody solution, the detection device detects no particles above the given particle size, or if further antigens which do not specifically react with the antibody used are assumed to be present in the sample, another antibody solution can next be introduced. Prior to this, any precipitates that had been detected may be rinsed away from the measuring cell if necessary.

The following examples serve to explain the present invention. A limitation of the scope of protection of the present invention to the subject matter of the examples, however, is in no way intended.

EXAMPLES

Example 1

BSE Blood Test

Cattle stocks in Germany number about 15 million. Two to three million BSE tests (ELISA and Western Blot) are annually performed in Germany on the brains of dead animals. At present, a BSE quick test (ELISA or Western Blot) takes 6-8 hours. With the method according to the invention the BSE pathogen can be detected in a live animal with just a drop of blood within two minutes, the costs are reduced to only a fraction.

Example 2

Checking Stored Blood for New Variant Creutzfeldt-Jakob Disease (nvCJD)

Several actions present themselves for protecting the population against imaginable risks of a nvCJD transmission via blood. The most promising step would be testing each blood donation for the infection, as with hepatitis and aids. However, the pathogen occurs in minute amounts in sick persons. No reliable tests exist in the prior art.

The method according to the invention is capable of detecting the pathogen in blood or in blood products.

Example 3

Applications in the Food Industry

Mycotoxins are highly toxic decomposition products of certain fungi. Mycotoxins are haptens and, therefore, can be detected both qualitatively and quantitatively with the measuring method described above.

For screening tests of, for example, entire shiploads of coffee, tea, flour, or nuts, a qualitative test that can be performed on the spot in about two minutes will be sufficient.

A meat sample must be tested for about 15 applicable hormones in order to find out whether an animal had been fattened illegally with hormones. Hormones, too, are haptens, and can be detected both qualitatively and quantitatively as well with the method according to the invention. Hormone tests are required as well in pregnancy tests and thyroid tests, for example.

Larger slaughterhouses process 2000-3000 cattle per month, hence about 50-100 random samples are necessary in order to uncover illegal fattening. At present, the price for a hormone test (including 15 different hormones) is 600 Euros per piece of meat. Therefore, only 5-10 random samples per month are tested in butcher's shops, far too little to uncover illegal fattening. In conversations with large slaughterhouses, interest was signaled to perform ten times as many tests costing less (about 60-70 Euros per piece of meat) based on the method according to the invention. Conventional hormone tests have no possibility to achieve this price.

Example 4

Detection of Pesticides

Tubulin monomers are small individual protein spherules growing to long chains by a reaction with the energy vector GTP. Inhibitors and other toxins hinder or prevent this chain growth. The individual chains become entangled to form ropelike structures, the so-called protofilaments. These protofilaments in turn join up to form microtubuli which play a decisive role in cell division. By interfering with the chain formation of the monomers, one can control cell division and kill the pest.

Conversely, this method also offers a possibility for detecting plant pesticide residues in food and, thus, provide enhanced consumer protection. The chain growth described above, and its prevention, are directly measurable with the method according to the invention.

The invention claimed is:

1. A method for the detection of antigen-antibody precipitate concentration which comprises:
   providing a sample that contains antigens with a given maximum particle size, the antigens having at least two antibody binding sites;
   providing a fluid containing antibodies that have a given maximum particle size;
   contacting the sample with the fluid containing the antibodies, which yields a reaction mixture where in the presence of antigens having at least two antibody binding sites the antibodies can form an antigen-antibody precipitate;
   directing a light beam through the reaction mixture;
   detecting a signal by measuring with a photodetector the extinction at the light-dark boundary of the cone of light that is produced when the light generated by the laser is passing through a measuring cell containing the reaction mixture, the signal strength depending on the antigen-antibody precipitate concentration.

2. The method according to claim 1, wherein the sample contains antigens with a concentration in the order of magnitude of femtograms or attograms per liter.

3. The method of claim 1 or 2, wherein the step of providing a sample that contains antigens having a given maximum particle size comprises:
  a) providing a liquid,
    introducing a sample component into the liquid, and
    separating antigens that exceed a given particle size, in order to obtain a sample fluid that contains only antigens having a given maximum particle size, or
  b) providing an aliquot of fluid that contains antigens having a given maximum particle size and
    introducing a second sample component into the liquid that contains antigens having a given maximum particle size, in order to obtain a sample that contains antigens having a given maximum particle size.

4. The method of claim 1 or 2, wherein the separation of the antigens having a size exceeding the given maximum particle size is effected by filtration, the filter having a pore size of 20-450 nm, or 100-300 nm, or 200 nm.

5. The method of claim 1 or 2, wherein antibodies comprise at least one of a monoclonal antibody and a polyclonal antibody.

6. The method of claim 1 or 2, wherein the antibody is selected from the group consisting of immunoglobulin G and immunoglobulin M.

7. The method of claim 1 or 2, wherein the method allows the quantity of antigens to be detected quantitatively or semi-quantitatively.

8. The method of claim 1 or 2, wherein, at a constant concentration of antibodies, the decrease of the measured signal is directly related to the concentration of antigens.

* * * * *